(12) United States Patent
Solem

(10) Patent No.: US 6,395,212 B1
(45) Date of Patent: May 28, 2002

(54) COVERED STENT AND METHOD OF MAKING IT

(76) Inventor: Jan Otto Solem, Nordmannavägen 20, 237 31 Bjärred (SE)

( * ) Notice: Subject to any disclaimer, the term of this patent is extended or adjusted under 35 U.S.C. 154(b) by 0 days.

(21) Appl. No.: 09/461,379

(22) Filed: Dec. 15, 1999

(30) Foreign Application Priority Data

Oct. 13, 1999 (SE) ................................. 9903674

(51) Int. Cl.[7] ............................ A61F 2/04; A61F 2/06; B29C 61/02
(52) U.S. Cl. ........................................... 264/230
(58) Field of Search .......................... 264/230

(56) References Cited

U.S. PATENT DOCUMENTS

| | | |
|---|---|---|
| 5,122,154 A | 6/1992 | Rhodes |
| 5,123,917 A | 6/1992 | Lee |
| 5,824,046 A | 10/1998 | Smith et al. |
| 5,922,393 A | 7/1999 | Jayaraman |
| 5,925,075 A | 7/1999 | Myers et al. |
| 5,928,279 A | 7/1999 | Shannon et al. |
| 6,010,529 A * | 1/2000 | Herweck et al. ......... 623/23.69 |
| 6,107,004 A * | 8/2000 | Donadio, III ............... 430/320 |
| 6,139,573 A * | 10/2000 | Sogard et al. ............. 623/1.13 |

FOREIGN PATENT DOCUMENTS

| | | |
|---|---|---|
| EP | 0 775 472 A2 | 5/1997 |
| WO | WO 96/28115 A1 | 9/1996 |
| WO | WO 98/26731 A2 | 6/1998 |
| WO | WO 98/33638 A1 | 8/1998 |

OTHER PUBLICATIONS

U.S. Patent & Trademark Office, Abstract of US. 5,922,393, issued Jul. 13, 1999.

* cited by examiner

Primary Examiner—Leo B. Tentoni
(74) Attorney, Agent, or Firm—Browdy and Neimark, P.L.L.C.

(57) ABSTRACT

A method of making a covered stent comprises the steps of producing a stent (1) having a diameter corresponding to an unexpanded state of the stent (1) and producing a tube (2) of a film material. The film material of the tube (2) should be shrinkable by exposure to an elevated temperature and the tube (2) should, before shrinking, have a greater diameter than the stent (1). As further steps of the method, the stent (1) is introduced into the tube (2), and the tube (2) is exposed to the elevated temperature for reducing the diameter of the tube (2) such that the stent (1) is affixed within the tube (2). The tube may be longer than the stent such that the ends of the tube may be introduced into the ends of the stent and affixed by short sections of a stent material. Collars may be formed at the ends of the tube and may also be covered by the film material.

35 Claims, 4 Drawing Sheets

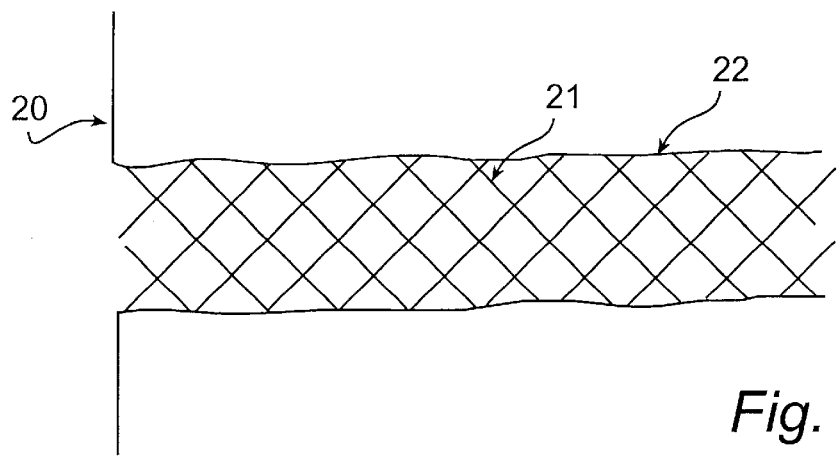
Fig. 12
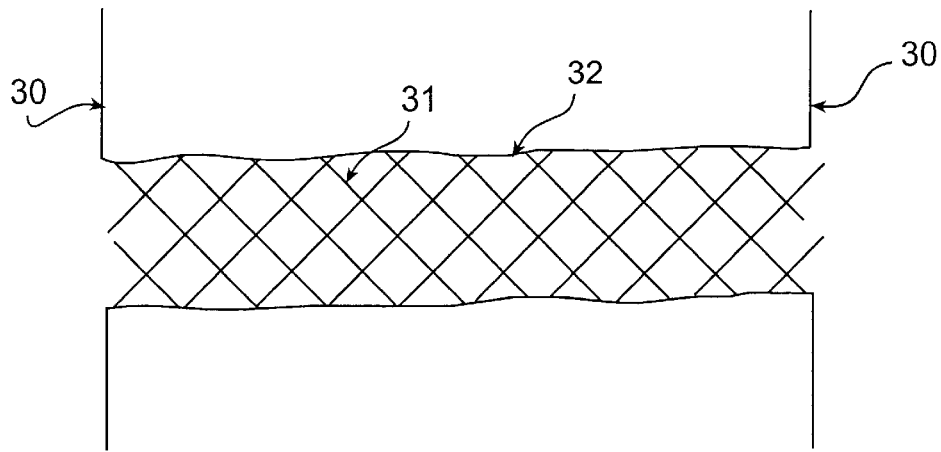
Fig. 13
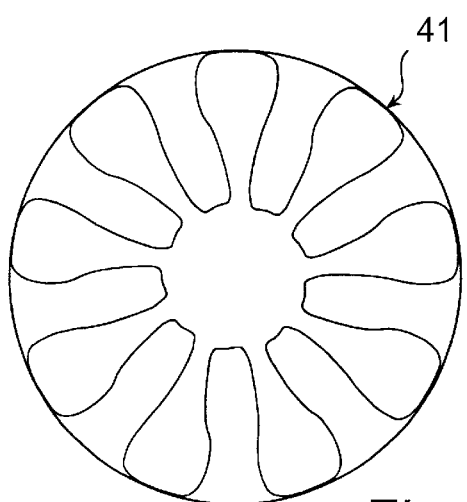 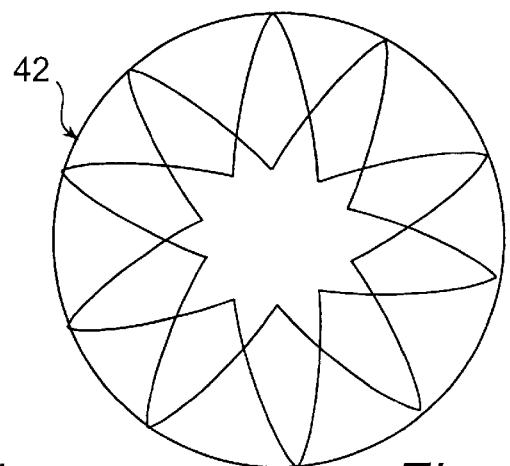
Fig. 14  Fig. 15

COVERED STENT AND METHOD OF MAKING IT

The present invention relates to covered stents and to methods of making covered stents.

Balloon dilatation of blocked blood vessels;, mainly arteries, is one of the most common interventions in medical practice today. Thus, every year one million such interventions are made only in the coronary arteries of the heart. In the peripheral arteries, the numbers are similar. In about 60% of the cases, a stent of petal grid is inserted to support the vessel wall after dilatation Many of these interventions with a balloon or other instruments in the arteries create injuries and/or perforations of the vessel wall causing bleeding. In other cases, the vessel has undergone a spontaneous rupture. In these cases of vessel lesions and perforations a cover on the metal stents may close the hole or cover the damage of the inner layer of the vessel, called intima.

In addition to this, one out of one thousand newborn children are born with serious malformations or defects of the heart or the great vessels that require heart surgery with or without the use of a heart and lung machine. Many of these operations have the purpose to create new anatomic connections between blood vessels or between blood vessels and the atria or chambers of the heart.

Some products of covered stents (or stented grafts) that exist today have a cover of extruded fluoropolymers, e.g. polytetrafluoroethylene (ePTFE), either as a sheet wrapped around the stent, placed between a double sandwich stent, or the polymers are moulded to the stent. All these methods have disadvantages. The double stent (sandwich) is stiff and thick and will not easily bend around the corners and the bends that are common in blood vessels. The moulded stent on the other hand are prone to get cracks, deliminations and leakages.

U.S. Pat. No. 5,122,154 (Rhodes) discloses an endovascular graft comprising an elongated tubular sleeve having a plurality of expandable, ring-like, stent sections located at equidistantly spaced positions along the sleeve. The sleeve is formed of a thin and highly flexible material, such as expanded polytetrafluoroethylene, and is pleated; i.e. includes a plurality of longitudinally extending pleats. The pleated tube is normally in a compacted state, that is each of the pleats overlies and abuts a contiguous portion of an immediately adjacent pleat. The tube is arranged to be expanded to an expanded state wherein its plates open up and form a generally continuous curved surface.

U.S. Pat. No. 5,824,046 (Smith, et al.) discloses a composite intraluminar device and a method of forming such a device. This method comprises providing an elongate radially expandable tubular stent. A stent cover is formed from a longitudinal segment of unsintered ePTFE having a first longitudinal expanse and a first transverse expanse. The segment is expanded along the transverse expanse to provide a second transverse expanse greater than the first transverse expanse and a second longitudinal expanse less than the first longitudinal expanse. Finally, the expanded segment is wrapped exteriorly about the stent, with the second transverse expanse extending longitudinally along the elongate stent. In order to fixate the segment to the stent, the opposed longitudinal ends of the segment are overlapped and secured together, e.g. by an adhesive.

U.S. Pat. No. 5,922,393 (Jayraman) discloses a coated stent, wherein the stent is made from a flat sheet, the ends of which are assembled together by surface fusing. A coating is attached to the stent only at a single area of line contact on the outer surface of the stent with the remainder of the coating being larger than the unexpanded stent. Alternatively, a "self-expanding" stent is placed in a container of coating material and is coated. Thereafter, the stent is programmed in a desired manner and is subsequently physically compressed and kept inside a sheath.

U.S. Pat. No. 5,925,075 (Myers, et al) discloses a tubular intraluminal graft in the form of a tubular diametrically adjustable stent having a tubular covering of porous expanded polytetrafluoroethylene which is less than 0.10 mm thick. This covering may be on the exterior surface of the stent, or on the interior surface of the stent, or both. The covering may be affixed to the stent by an adhesive, which is preferably fluorinated ethylene propylene. The covering is affixed to the stent in its expanded state and the stent is then compressed mechanically to reduce the diameter of the covered stent. The resulting collapsed stent may then be expanded, e.g. by being heated.

U.S. Pat. No. 5,928,279 discloses further stented, radially expandable, tubular PTFE grafts manufactured by the individual components of the stented grafts being preassembled on a mandrel and subsequently heated to facilitate attachment of the PTFE layer(s) on one another and/or to the stent.

An object of the present invention is to provide a simplified method of making a covered stent and, more specifically, a flexible covered stent that will easily follow around the bends of blood vessels and also a stent that is not prone to get cracks, deliminations and leakages.

This object is attained by the method disclosed below and by the covered stent obtained thereby. Preferred alternatives of this method are also disclosed below.

Thus, a method of making a covered stent comprises the steps of producing a stent having a diameter corresponding to a substantially unexpanded state of the stent producing a tube of a film material which is shrinkable by exposure to an elevated temperature, the tube having a greater diameter than said stent; introducing the stent into the tube; and exposing the tube to the elevated temperature for reducing the diameter of the tube such that the stent is affixed in the tube.

Fluorinated ethylene-propylene (FEP) and polytetrafluoroethylene (PTFE) have the characteristic that they will shrink when they are exposed to high temperatures. Heating above 260° C. for PTFE and above 200° C. for FEP will make an extruded tube to shrink with a ratio of four to one. This means that a 4 mm in diameter PTFE tube will shrink to a diameter of 1 mm. The same tube may later again be dilated to its previous diameter of 4 mm under room or body temperatures, for instance during a balloon dilatation of a human blood vessel.

A special feature of the new covered stent is the option of a collar in one or both ends of the device for the purpose of anchoring of the device and for sealing purposes.

The covered stent may also be supplied with internal stents, preferably made of a memory metal (e.g. Nitinol) self-expanding material that will affix the PTFE cover. In this case, the cover is turned around the edge to the inside of the stent instead of creating a collar that goes outwards. This turning inside of the cover will strengthen its attachment to the stent and prevent a peel-off of the cover, this is especially important if the device is implanted into big vessels with a high pressure, like the aorta.

The presented method of covering the stents may be used on any alloy or polymer of stents and combinations of different types of alloy and polymer. This includes the use of any self-expanding metal of a memory metal like the Nitinol alloy, or different types of memory polymers.

Percutaneous insertion of the covered stent (by puncture and catheter technique) made according to the present invention may replace many pediatric heart operations and coronary artery bypass surgical procedures.

Further objects and advantages of the invention will become apparent to those skilled in the art upon reading and understanding the following detailed description and the accompanying drawings.

FIGS. 9–15 illustrates further embodiments of a covered stent made according to the method of the present invention.

Figure 1:
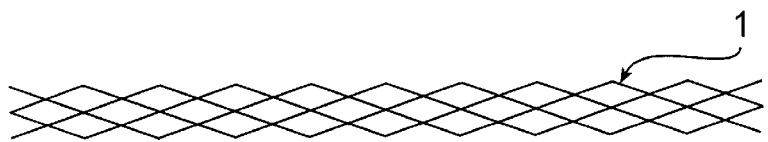
FIGS. 1–5 illustrate the steps of making a covered stent according to one embodiment of the present invention.

In FIG. 1, a stent 1 is shown in an unexpanded state, i.e. in a state having a first diameter, which is smaller than a second diameter that the stent will have in an expanded state. The stent may be any type of stent, e.g. made from a metal or a polymer.

Figure 2:
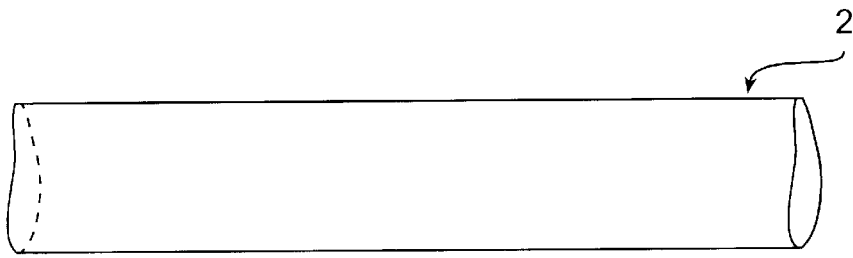

In FIG. 2, a tube 2 is shown which is made from a film of a material, which may be shrinked, by being heated. Preferably, the tube 2 is an extruded tube, but it may be formed into a tube from a film sheet. The diameter of the tube 2 is greater than the diameter of the stent 1 in its unexpanded state.

Figure 3:
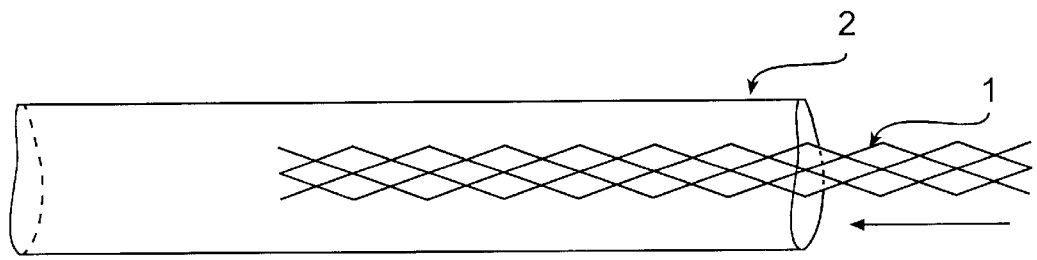
Figure 4:
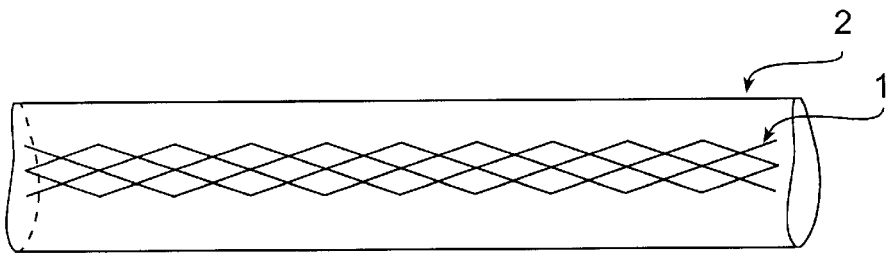
Figure 5:
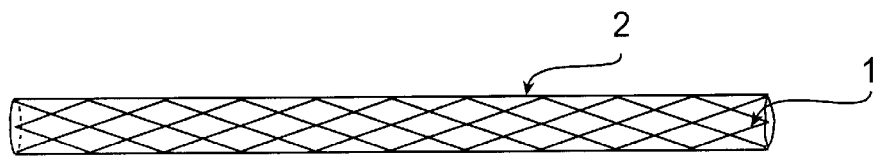

As illustrated in FIG. 3, the stent 1 is introduced into the tube 2 and, when fully positioned within the tube 2, as shown in FIG. 4, the temperature of the tube 2 is elevated such that shrinkage thereof is initiated. This shrinkage is preferably so dimensioned that the final diameter of the tube 2, and thus the stent 1, will be slightly less than the diameter of the stent 1 before being introduced into the tube 2, as shown in FIG. 5.

As a consequence, the stent 1 will be affixed within the tube 2 without the use of an adhesive or any other separate fixating means. When using a flexible stent 1 and a thin film in the tube 2, the combined stent 1 and tube 2 (i.e. the covered stent 1, 2) will still be almost as flexible as the original stent 1.

Figure 6:
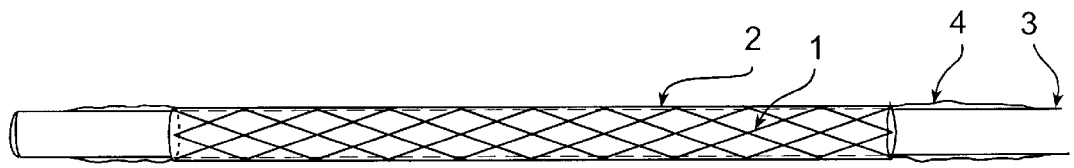
FIGS. 6–8 illustrate the steps of applying the covered stent in a blood vessel.

FIG. 6 illustrates the use of a conventional catheter 3 with a distal balloon 4 introduced into the stent 1 for expanding the stent 1 as well as the tube 2 enclosing the stent 1.

Figure 7:
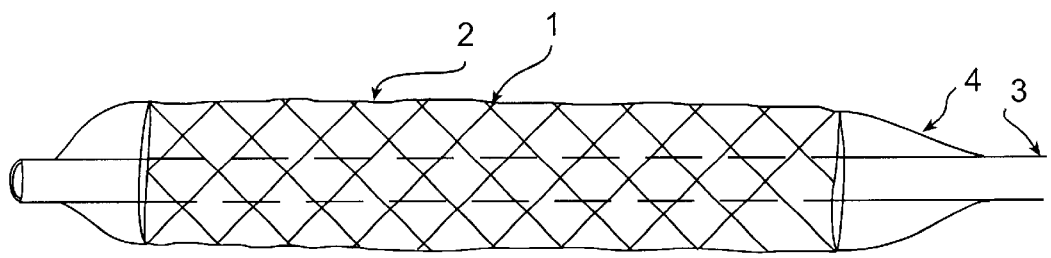

FIG. 7 illustrates the inflated balloon 4 that has transferred the stent 1 into its expanded state and also has expanded the tube 2, which still is in an affixed contact with the stent 1.

FIG, 8 finally shows the covered stent 1, 2 when the balloon 4 has been retracted therefrom.

Figure 8:
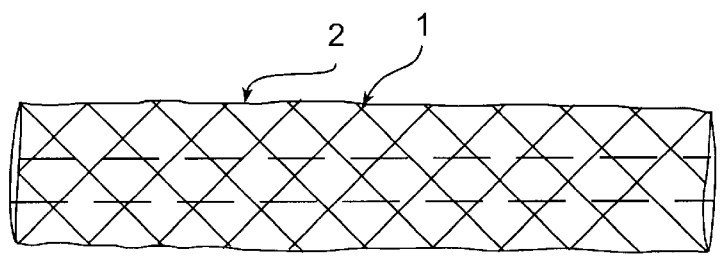

The steps shown in FIGS. 7 and 8 should of course be performed in a vessel (not shown) to be dilated.

Figure 9:
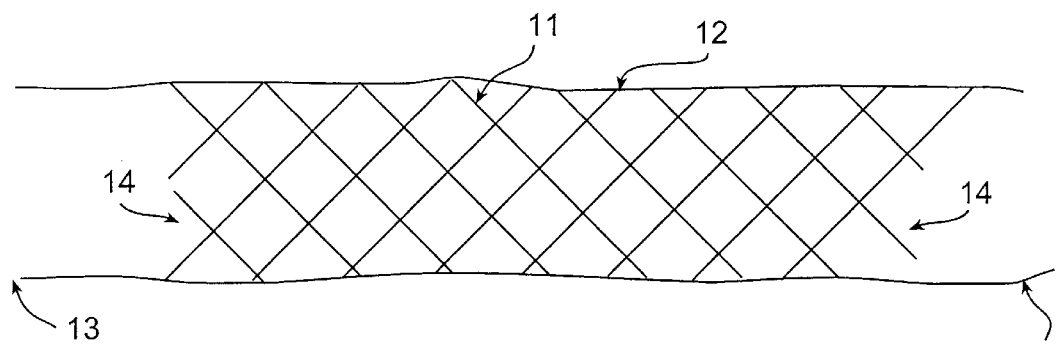
Figure 10:
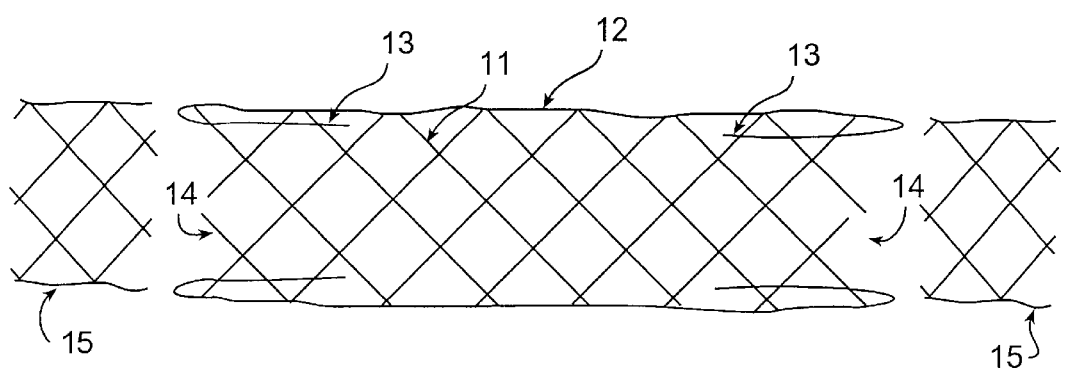
Figure 11:
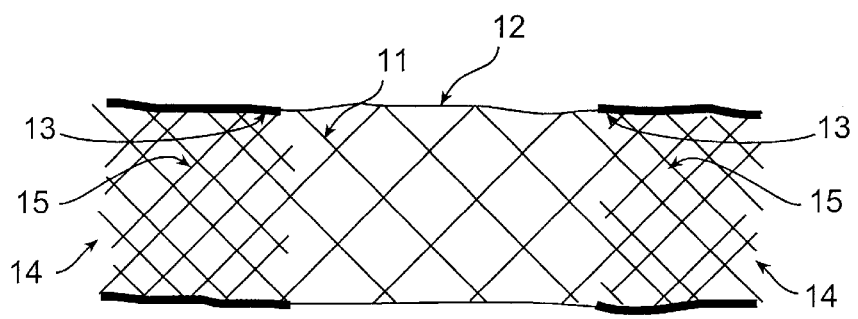

FIGS. 9–11 illustrate a second embodiment off a covered stent 11, 12 (i.e. a stent 11 combined with a shrinked tube 12) according to the present invention. Here the shrinked tube 12 is longer than the stent 11, such that, following the steps shown in FIGS. 1–5, the ends 13 of the tube 12 project outside of the ends 14 of the stent 11. Then, the projecting ends 13 of the tube 12 are inserted into the ends 14 of the stent 11, as shown in FIG. 10. Finally, short cylinder sections 15, shown in FIG. 10 outside the ends 14 of the stent 11 and made of a stent material, e.g. a self-expanding stent material, are inserted into the ends 14 of the stent 11. Thereby, the positions of the inserted ends 13 of the tube 12 are affixed within the ends 14 of the stent 11, as shown in FIG. 11.

FIGS. 12 and 13 illustrate further embodiments of a covered stent according to the present invention. In FIG. 12, a collar 20 is formed at one end of a covered stent 21, 22 (i.e. a stent 21 combined with a shrinked tube 22). In FIG. 13, collars 30 are formed at both ends of a covered stent 31, 32 (i.e. a stent 31 combined with a shrinked tube 32). The collars 20, 30 comprise a radially extending flange 41 or 42 made of a stent material, as illustrated in FIGS. 14 and 15, respectively. The flanges 41 and 42 preferably are covered by the same type of film material that covers the stent 21, 31, i.e. the tube 22, 32 may have extensions covering the flanges 41 and 42 when being shrinked. The tube 22, 32 may also end close to the flanges 41 and 42, which are not covered in that case. However, the film material preferably covers both sides of the flanges 41 and 42.

Using covered vascular stents according to the present invention will make the following procedures possible.

1. Coronary artery by-pass grafting.
2. Creation of a Glenn-shunt between the superior vena cava and the pulmonary artery by means of direct cannulation, penetration and insertion of the new covered stent with or without one or two collars.
3. Completion of the Fontan procedure after a previous Glenn shunt by insertion of the new covered stent with or without one or two collars.
4. Extra-anatomic creation of a new pulmonary artery between the right ventricle of the heart and the pulmonary artery in the cases of pulmonary atresia by means of insertion of the new covered stent with or without one or two collars and with or without a valve.
5. Creation of new extra-anatomic vascular connections in the cases of hypoplastic left heart syndrome, or other congenital heart disorders.
6. Creation of a Blalock-Thausing shunt between the subclavian artery and the pulmonary artery.
7. Subintimal channelling.

It is to be understood that modifications of the above-described methods and covered stents can be made by people skilled in the art without departing from the spirit and scope of the invention.

What is claimed is:

1. A method of making a covered stent comprising the steps of:
    producing a stent having a diameter corresponding to a substantially unexpanded state of the stent;
    producing a tube of a film material, which is shrinkable by exposure to an elevated temperature, the tube having a greater diameter and a longer length than said stent;
    introducing the stent into the tube;
    exposing the tube to the elevated temperature for reducing the diameter of the tube such that the stent is affixed within the tube; and
    inserting projecting ends of the tube into the ends of the stent.

2. A method according to claim 1, wherein the tube (2; 12; 22; 32) is produced by extrusion of a shrinkable film material.

3. A method according to claim 1, wherein the shrinkable film material is fluorinated ethylene-propylene.

4. A method according to claim 1, wherein a short cylinder section (15) of a stent material is introduced into each one of the ends (13) of the tube (12) inserted into the ends (14) of the stent (11).

5. A method according to claim 4, wherein the stent material is a self-expanding stent material.

6. A method according to claim 1, wherein a collar (20; 30) is formed at least one of the ends of the stent (21; 31).

7. A method according to claim 6, wherein the collar (20; 30) is formed by the stent material of the stent (21; 31).

8. A method according to claim 7, wherein the collar (20; 30) is covered on at least one side by the film material of the tube (22; 32).

9. A method according to claim 1, wherein the shrinkable film material is polytetrafluoroethylene.

10. A method according to claim 1, wherein the step of producing a stent comprises producing a self-expandable stent.

11. A method according to claim 10, wherein the step of producing a self-expandable stent comprises the step of producing a stent of a self-expanding metal.

12. A method according to claim 10, wherein the step of producing a self-expandable stent comprises the step of producing a stent of a memory polymer.

13. A method according to claim 1, wherein the ends of the tube are inserted into the ends of the stent such that the inside if the stent is only partly covered.

14. A method of making a covered stent comprising the steps of:

producing a stent having a diameter corresponding to a substantially unexpanded state of the stent;

producing a tube of a film material, which is shrinkable by exposure to an elevated temperature, the tube having a greater diameter than said stent;

forming a collar at least at one of the ends of the stent;

introducing the stent into the tube; and exposing the tube to the elevated temperature for reducing the diameter of the tube such that the stent is affixed within the tube.

15. A method according to claim 14, wherein the step of producing a stent comprises producing a self-expandable stent.

16. A method according to claim 15, wherein the step of producing a self-expandable stent comprises the step of producing a stent of a self-expanding metal.

17. A method according to claim 15, wherein the step of producing a self-expandable stent comprises the step of producing a stent of a memory polymer.

18. A method according to claim 14, wherein the tube is produced by extrusion of a shrinkable film material.

19. A method according to claim 18, wherein the shrinkable film material is fluorinated ethylene-propylene.

20. A method according to claim 18, wherein the shrinkable film material is polytetrafluoroethylene.

21. A method according to claim 14, wherein the tube is made longer than the stent and projecting ends of the tube are inserted into the ends of the stent affixed in the tube.

22. A method according to claim 21, wherein a short cylinder section of a stent material is introduced into each one of the ends of the tube inserted into the ends of the stent.

23. A method according to claim 22, wherein the stent material is a self-expanding stent material.

24. A method according to claim 14, wherein the collar is formed by the stent material of the stent.

25. A method according to claim 24, wherein the collar is covered on at least one side by the film material of the tube.

26. A method of making a covered stent comprising the steps of:

producing a stent having a diameter corresponding to a substantially unexpanded state of the stent;

producing a tube of a film material, which is shrinkable by exposure to an elevated temperature, the tube having a greater diameter than said stent;

introducing the stent into the tube; and exposing the tube to the elevated temperature for reducing the diameter of the tube such that the stent is affixed within the tube and no film material is disposed within the stent.

27. A method according to claim 26, wherein the step of producing a stent comprises producing a self-expandable stent.

28. A method according to claim 27, wherein the step of producing a self-expandable stent comprises the step of producing a stent of a self-expanding metal.

29. A method according to claim 27, wherein the step of producing a self-expandable stent comprises the step of producing a stent of a memory polymer.

30. A method according to claim 26, wherein the tube is produced by extrusion of a shrinkable film material.

31. A method according to claim 26, wherein the shrinkable film material is fluorinated ethylene-propylene.

32. A method according to claim 26, wherein the shrinkable film material is polytetrafluoroethylene.

33. A method according to claim 26, wherein a collar is formed at least one of the ends of the stent.

34. A method according to claim 33, wherein the collar is formed by the stent material of the stent.

35. A method according to claim 34, wherein the collar is covered on at least one side by the film material of the tube.

* * * * *